United States Patent
Urelli

Patent Number: 5,657,488
Date of Patent: Aug. 19, 1997

[54] DECUBITUS PAD SYSTEM

[76] Inventor: Virginia Urelli, 411 NW. 32 Ct., Miami, Fla. 33125

[21] Appl. No.: 567,050

[22] Filed: Dec. 4, 1995

[51] Int. Cl.$^6$ .............................. A41D 13/00; A61F 13/00
[52] U.S. Cl. ........................ 2/456; 602/61; 2/467
[58] Field of Search ........................... 2/22, 2; 602/60, 602/61; 128/888, 889, 892, 894

[56] References Cited

U.S. PATENT DOCUMENTS

| | | | |
|---|---|---|---|
| D. 225,472 | 12/1972 | Lowrey | 128/889 |
| 2,056,767 | 10/1936 | Blath | 128/889 |
| 2,085,296 | 6/1937 | Carey | 128/889 |
| 2,706,476 | 4/1955 | Diamond | 128/889 |
| 3,158,878 | 12/1964 | Pernell | 128/889 |
| 3,556,096 | 1/1971 | Fuller | 128/888 |
| 4,567,887 | 2/1986 | Couch, Jr. | 128/889 |
| 5,451,201 | 9/1995 | Prengler | 602/13 |

*Primary Examiner*—Bibhu Mohanty

[57] ABSTRACT

A decubitus pad system includes a peripheral padding positionable about a decubitus ulcer. The padding has an interior layer and an exterior layer. The interior layer has a plurality of foam supports secured thereto. The padding has a plurality of openings formed through the interior layer and the exterior layer adjacent to the foam supports whereby the plurality of foam supports surrounding each of the plurality of openings whereby the plurality of openings are positioned over a bedsore of a patient.

1 Claim, 4 Drawing Sheets

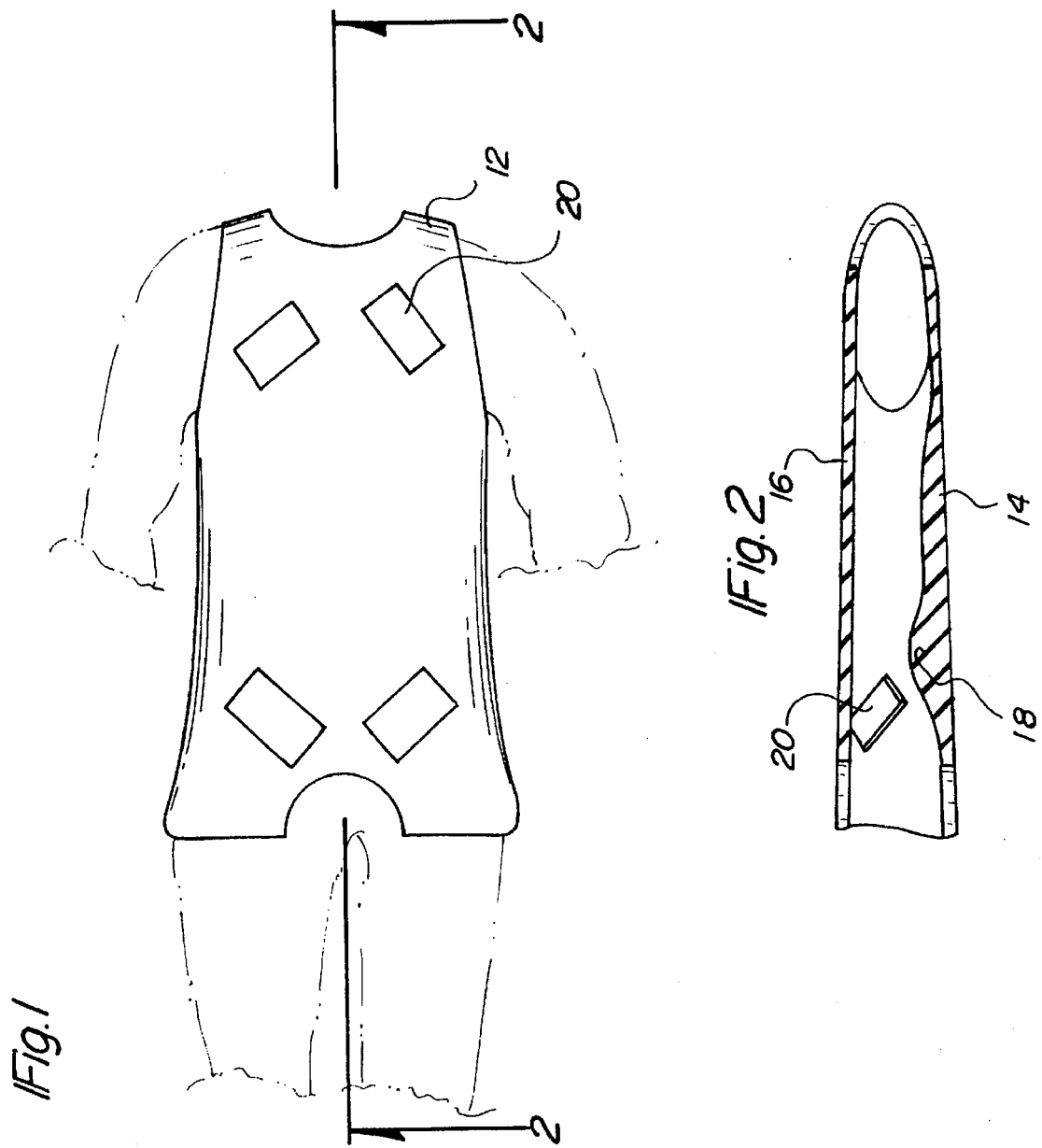

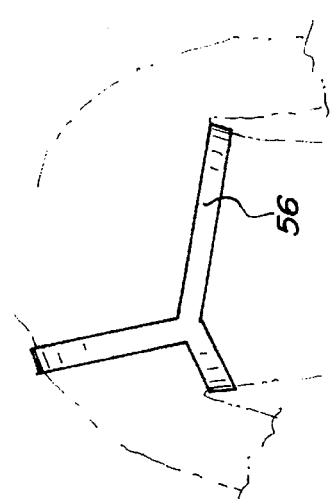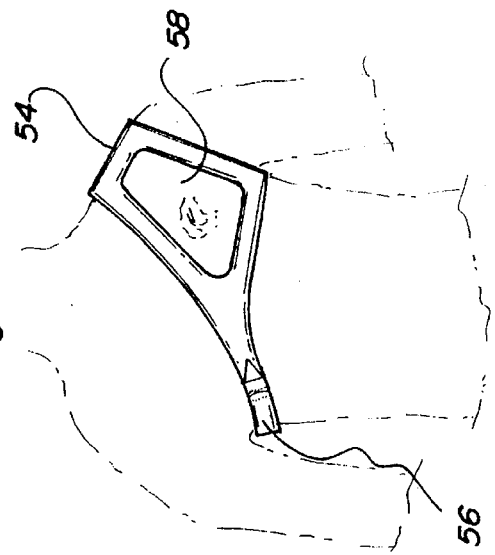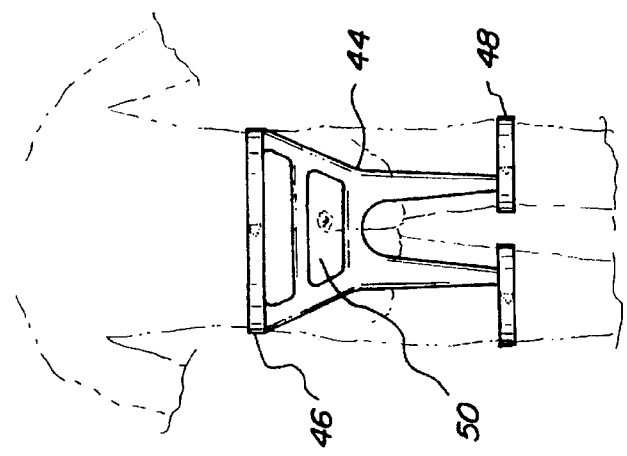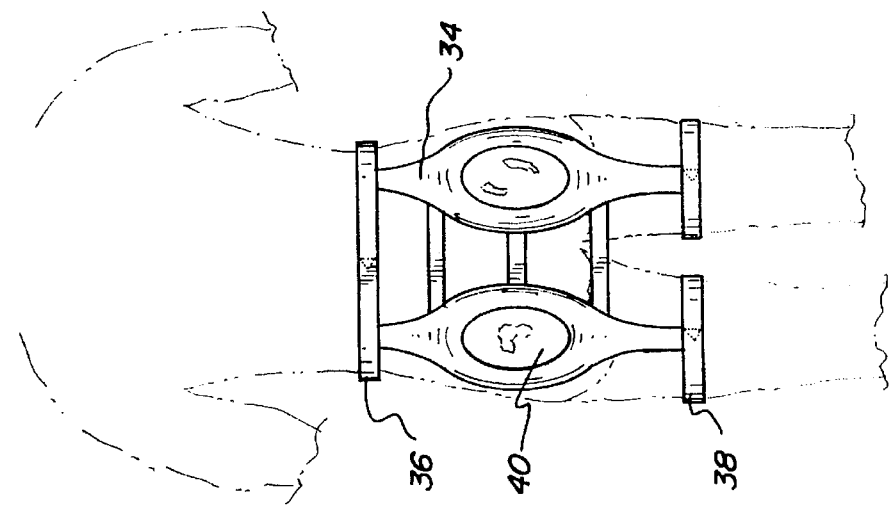

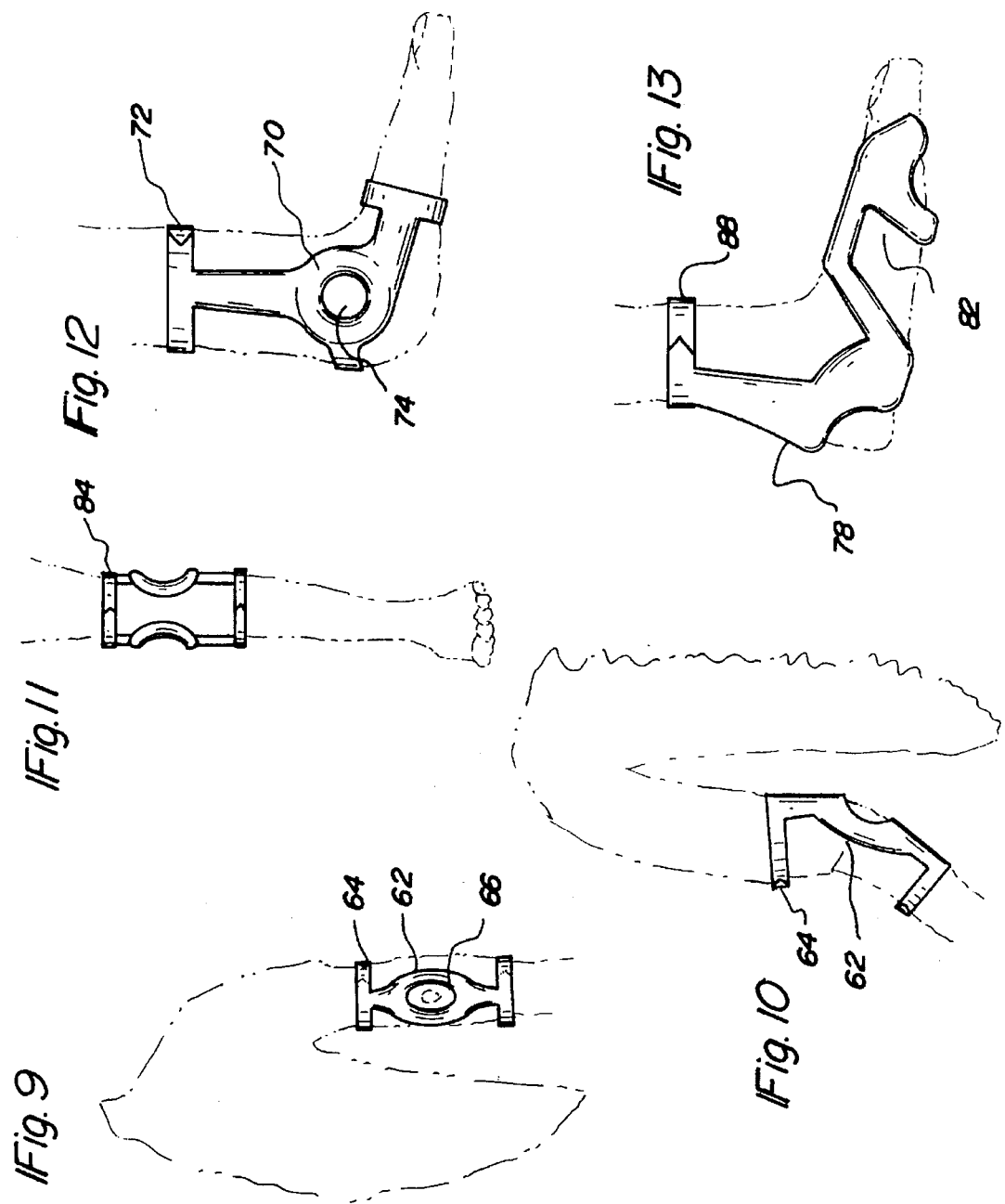

DECUBITUS PAD SYSTEM

BACKGROUND OF THE INVENTION

1. Field of the Invention

The present invention relates to a decubitus pad system and more particularly pertains to providing a peripheral padding positionable about a decubitus ulcer with a decubitus pad system.

2. Description of the Prior Art

The use of decubitus cushions is known in the prior art. More specifically, decubitus cushions heretofore devised and utilized for the purpose of protecting against development of bedsores are known to consist basically of familiar, expected and obvious structural configurations, notwithstanding the myriad of designs encompassed by the crowded prior art which have been developed for the fulfillment of countless objectives and requirements.

By way of example, U.S. Pat. No. 4,643,481 to Saloff et al. discloses a seat system for preventing decubiti.

U.S. Pat. No. 4,620,337 to Williams et al. discloses a convoluted support pad for prevention of decubitus ulcers and apparatus for making same.

U.S. Pat. No. 3,937,218 to Gaylord, Jr. discloses a decubitus pad.

U.S. Pat. No. 3,721,232 to Trenchard discloses a surgical pad method for decubitus ulcer management.

U.S. Pat. No. 4,425,676 to Crane discloses a cushion to reduce the incidence of decubitus ulcers in immobilized patients.

U.S. Pat. No. 4,255,824 to Pertchik discloses a cushion for decubitus ulcers.

While these devices fulfill their respective, particular objective and requirements, the aforementioned patents do not describe a decubitus pad system for providing a peripheral padding positionable about a decubitus ulcer.

In this respect, the decubitus pad system according to the present invention substantially departs from the conventional concepts and designs of the prior art, and in doing so provides an apparatus primarily developed for the purpose of providing a peripheral padding positionable about a decubitus ulcer.

Therefore, it can be appreciated that there exists a continuing need for new and improved decubitus pad system which can be used for providing a peripheral padding positionable about a decubitus ulcer. In this regard, the present invention substantially fulfills this need.

SUMMARY OF THE INVENTION

In the view of the foregoing disadvantages inherent in the known types of decubitus cushions now present in the prior art, the present invention provides an improved decubitus pad system. As such, the general purpose of the present invention, which will be described subsequently in greater detail, is to provide a new and improved decubitus pad system and method which has all the advantages of the prior art and none of the disadvantages.

To attain this, the present invention essentially comprises a body suit having an interior layer and an exterior layer. The interior layer has a plurality of foam supports secured thereto. The body suit has a plurality of openings formed through the interior layer and the exterior layer adjacent to the foam supports whereby the plurality of foam supports surround each of the plurality of openings. The body suit is adapted for securement to a torso of a patient. The device includes a leg and hip portion having an upper securement strap securable around a waist of a patient. The leg and hip portion has a pair of leg securement portions adapted for securement around legs of a patient. The leg and hip portion has an interior layer and an exterior layer. The interior layer has a plurality of foam supports secured thereto. The leg and hip portion has an opening formed through the interior layer and the exterior layer adjacent to the foam supports whereby the plurality of foam supports surround the opening. The device includes a backside portion having an upper securement strap securable around a waist of a patient. The backside portion has a pair of leg securement portions adapted for securement around legs of a patient. The backside portion has an interior layer and an exterior layer. The interior layer has a plurality of foam supports secured thereto. The backside portion has a pair of openings formed through the interior layer and the exterior layer adjacent to the foam supports whereby the plurality of foam supports surround the openings. The device includes a frontside portion having an upper securement strap securable around a waist of a patient. The frontside portion has a pair of leg securement portions adapted for securement around legs of a patient. The frontside portion has an interior layer and an exterior layer. The interior layer has a plurality of foam supports secured thereto. The frontside portion has a pair of openings formed through the interior layer and the exterior layer adjacent to the foam supports whereby the plurality of foam supports surround the openings. The device includes a shoulder portion having a securement strap securable around a torso of a patient. The shoulder portion has an interior layer and an exterior layer. The interior layer has a plurality of foam supports secured thereto. The shoulder portion has an opening formed through the interior layer and the exterior layer adjacent to the foam supports whereby the plurality of foam supports surround the opening. The device includes an elbow portion having securement straps securable around an arm of a patient. The elbow portion has an interior layer and an exterior layer. The interior layer has a plurality of foam supports secured thereto. The elbow portion has an opening formed through the interior layer and the exterior layer adjacent to the foam supports whereby the plurality of foam supports surround the opening. The device includes an ankle portion having securement straps securable around a lower leg and foot of a patient. The ankle portion has an interior layer and an exterior layer. The interior layer has a plurality of foam supports secured thereto. The ankle portion has an opening formed through the interior layer and the exterior layer adjacent to the foam supports whereby the plurality of foam supports surrounding the opening. The device includes a foot portion having a securement strap securable around a lower leg of a patient. The foot portion has an interior layer and an exterior layer. The interior layer has a plurality of foam supports secured thereto. The foot portion has an opening formed through the interior layer and the exterior layer adjacent to the foam supports whereby the plurality of foam supports surround the opening.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved decubitus pad system which has all the advantages of the prior art decubitus cushions and none of the disadvantages.

It is another object of the present invention to provide a new and improved decubitus pad system which may be easily and efficiently manufactured and marketed.

It is a further object of the present invention to provide a new and improved decubitus pad system which is of durable and reliable construction.

An even further object of the present invention is to provide a new and improved decubitus pad system which is susceptible of a low cost of manufacture with regard to both materials and labor, and which accordingly is then susceptible of low prices of sale to the consuming public, thereby making such a decubitus pad system economically available to the buying public.

Still yet another object of the present invention is to provide a new and improved decubitus pad system which provides in the apparatuses and methods of the prior art some of the advantages thereof, while simultaneously overcoming some of the disadvantages normally associated therewith.

Even still another object of the present invention is to provide a new and improved decubitus pad system for providing a peripheral padding positionable about a decubitus ulcer.

Lastly, it is an object of the present invention to provide a new and improved decubitus pad system includes a peripheral padding positionable about a decubitus ulcer. The padding has an interior layer and an exterior layer. The interior layer has a plurality of foam supports secured thereto. The padding has a plurality of openings formed through the interior layer and the exterior layer adjacent to the foam supports whereby the plurality of foam supports surrounding each of the plurality of openings whereby the plurality of openings are positioned over a bedsore of a patient.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the decubitus pad system constructed in accordance with the principles of the present invention.

FIG. 2 is a cross-sectional view as taken along line 2—2 of FIG. 1.

FIG. 5 is a front view of the backside device of the present invention.

FIG. 6 is a front view of the front side device of the present invention.

FIG. 7 is a back view of the shoulder device of the present invention.

FIG. 8 is a front view of the shoulder device of the present invention.

FIG. 9 is a front view of the elbow pad of the present invention.

FIG. 10 is a side view of the elbow pad of the present invention.

FIG. 11 is a front view of the knee pad of the present invention.

FIG. 12 is a side view of the ankle pad of the present invention.

FIG. 13 is a side view of the foot pad of the present invention.

The same reference numerals refer to the same parts through the various Figures.

DESCRIPTION OF THE PREFERRED EMBODIMENT

Figure 3:
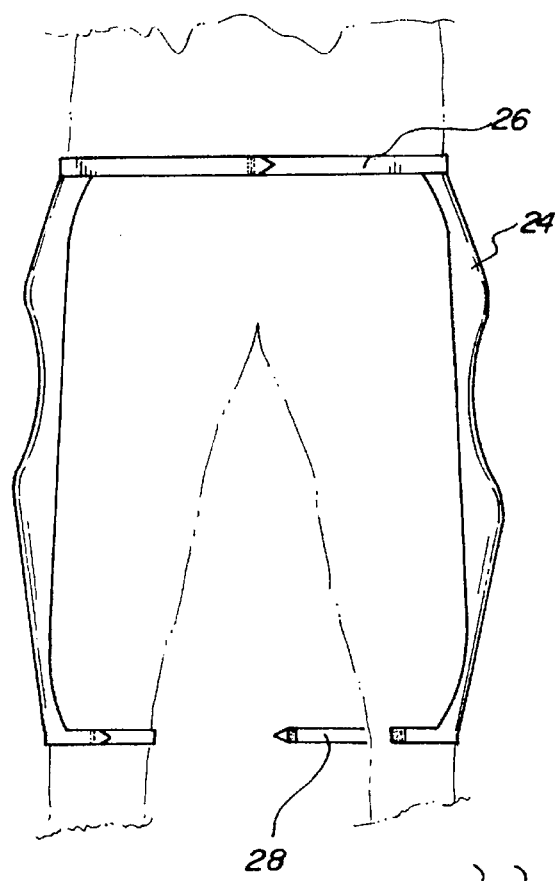
FIG. 3 is a front view of the leg and hip portion of the present invention in place on a person.

With reference now to the drawings, and in particular, to FIGS. 1–13 thereof, the preferred embodiment of the new and improved decubitus pad system embodying the principles and concepts of the present invention and generally designated by the reference number 10 will be described.

Specifically, it will be noted in the various Figures that the device relates to a new and improved decubitus pad system for providing a peripheral padding positionable about a decubitus ulcer. In its broadest context, the device consists of a body suit, a hip and leg portion, a backside portion, a frontside portion, a shoulder portion, an elbow portion, a knee portion, an ankle portion, a foot portion. Such components are individually configured and correlated with respect to each other so as to attain the desired objective.

FIGS. 1 and 2 illustrate a body suit 12 having an interior layer 14 and an exterior layer 16. The interior layer 14 has a plurality of foam supports 18 secured thereto. The body suit 12 has a plurality of openings 20 formed through the interior layer 14 and the exterior layer 16 adjacent to the foam supports 18 whereby the plurality of foam supports 18 surround each of the plurality of openings 20. The body suit 12 is adapted for securement to a torso of a patient. The body suit 12 is positioned over the torso of the patient and the openings 20 are cut out where bedsores are present on the torso. Thus, when the patient is laying down, the foam supports 18 around the openings 20 abut the bed surface thereby preventing contact with the bedsores.

Figure 4:
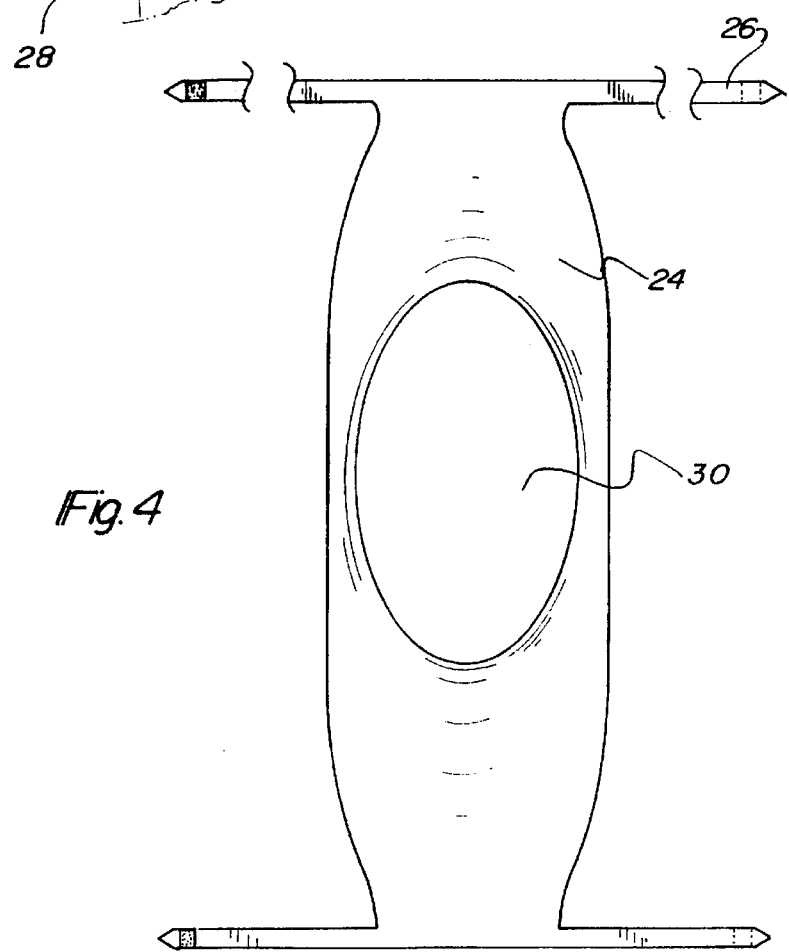
FIG. 4 is a front view of the leg and hip portion of the present invention.

Next, the device 10 includes a leg and hip portion 24 illustrated in FIGS. 3 and 4. The leg and hip portion 24 has an upper securement strap 26 securable around a waist of a patient. The leg and hip portion 24 has a pair of leg securement portions 28 adapted for securement around legs of a patient. The leg and hip portion 24 has an interior layer 14 and an exterior layer 16. The interior layer 14 has a plurality of foam supports 18 secured thereto. The leg and hip portion 24 has an opening 30 formed through the interior layer 14 and the exterior layer 16 adjacent to the foam supports 18 whereby the plurality of foam supports 18 surround the opening 30. The leg and hip portion 24 protect against bedsores on the hips and sides of the legs of a patient.

The device 10 includes a backside portion 34, illustrated in FIG. 5, having an upper securement strap 36 securable around a waist of a patient. The backside portion 34 has a pair of leg securement portions 38 adapted for securement around legs of a patient. The backside portion 34 has an interior layer 14 and an exterior layer 16. The interior layer 14 has a plurality of foam supports 18 secured thereto. The backside portion 34 has a pair of openings 40 formed through the interior layer 14 and the exterior layer 16 adjacent to the foam supports 18 whereby the plurality of foam supports 18 surround the openings 40. The pair of openings 40 are positioned over bedsores of the buttocks of a patient.

The device 10 includes a frontside portion 44, illustrated in FIG. 6, having an upper securement strap 46 securable around a waist of a patient. The frontside portion 44 has a pair of leg securement portions 48 adapted for securement around legs of a patient. The frontside portion 44 has an interior layer 14 and an exterior layer 16. The interior layer 14 has a plurality of foam supports 18 secured thereto. The frontside portion 44 has a pair of openings 50 formed through the interior layer 14 and the exterior layer 16 adjacent to the foam supports 18 whereby the plurality of foam supports 18 surround the openings 50. The openings 50 are arranged with one above the other to protect bedsores on a lower stomach area or on a lower back area of the patient.

The device 10 includes a shoulder portion 54, illustrated in FIGS. 7 and 8, having a securement strap 56 securable around a torso of a patient. The shoulder portion 54 has an interior layer 14 and an exterior layer 16. The interior layer 14 has a plurality of foam supports 18 secured thereto. The shoulder portion 54 has an opening 58 formed through the interior layer 14 and the exterior layer 16 adjacent to the foam supports 18 whereby the plurality of foam supports 18 surround the opening 58. The opening 58 protects bedsores on a back shoulder or a pectoral area of the patient.

The device 10 includes an elbow portion 62, illustrated in FIGS. 9 and 10, having securement straps 64 securable around an arm of a patient. The elbow portion 62 has an interior layer 14 and an exterior layer 16. The interior layer 14 has a plurality of foam supports 18 secured thereto. The elbow portion 62 has an opening 66 formed through the interior layer 14 and the exterior layer 16 adjacent to the foam supports 18 whereby the plurality of foam supports 18 surround the opening 66. The opening 66 protects bedsores on a patient's elbow.

The device 10 includes an ankle portion 70, illustrated in FIG. 12 having securement straps 72 securable around a lower leg and foot of a patient. The ankle portion 70 has an interior layer 14 and an exterior layer 16. The interior layer 14 has a plurality of foam supports 18 secured thereto. The ankle portion 70 has an opening 74 formed through the interior layer 14 and the exterior layer 16 adjacent to the foam supports 18 whereby the plurality of foam supports 18 surround the opening 74. The opening 74 protects bedsores on a patient's ankle.

Lastly, the device 10 includes a foot portion 78, illustrated in FIG. 13 having a securement strap 80 securable around a lower leg of a patient. The foot portion 78 has an interior layer 14 and an exterior layer 16. The interior layer 14 has a plurality of foam supports 18 secured thereto. The foot portion 78 has an opening 82 formed through the interior layer 14 and the exterior layer 16 adjacent to the foam supports 18 whereby the plurality of foam supports 18 surround the opening 82. The opening 82 protects bedsores on a patient's feet. Additional items could be constructed to protect other body parts of a patient from the commonly occurring problem of developing bedsores. FIG. 11 illustrates a knee pad 84 from protection of bedsores in that area of the body.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and the manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modification and changes will readily occur to those skilled in the art, it is not desired to limit the invention to the exact construction and operation shown and described, and accordingly, all suitable modification and equivalents may be resorted to, falling within the scope of the invention.

What is claimed as being new and desired to be protected by LETTERS PATENT of the United States is as follows:

1. A decubitus pad system for providing a peripheral padding positionable about a decubitus ulcer comprising, in combination:

a body suit covering substantially the entire torso area having an interior layer and an exterior layer, the interior layer having a plurality of foam supports secured thereto, the body suit having a plurality of openings formed through the interior layer and the exterior layer adjacent to the foam supports whereby the plurality of foam supports surround each of the plurality of openings, the body suit adapted for securement to a torso of a patient;

a leg and hip portion having an upper securement strap securable around a waist of a patient, the leg and hip portion having a pair of leg securement portions adapted for securement around legs of a patient, the leg and hip portion having an interior layer and an exterior layer, the interior layer having a plurality of foam supports secured thereto, the leg and hip portion having an opening formed through the interior layer and the exterior layer adjacent to the foam supports whereby the plurality of foam supports surround the opening;

a backside portion having an upper securement strap securable around a waist of a patient, the backside portion having a pair of leg securement portions adapted for securement around legs of a patient, the backside portion having an interior layer and an exterior layer, the interior layer having a plurality of foam supports secured thereto, the backside portion having a pair of openings formed through the interior layer and the exterior layer adjacent to the foam supports whereby the plurality of foam supports surround the openings;

a frontside portion having an upper securement strap securable around a waist of a patient, the frontside portion having a pair of leg securement portions adapted for securement around legs of a patient, the frontside portion having an interior layer and an exterior layer, the interior layer having a plurality of foam supports secured thereto, the frontside portion having a pair of openings formed through the interior layer and the exterior layer adjacent to the foam supports whereby the plurality of foam supports surround the openings;

a shoulder portion having a securement strap securable around a torso of a patient, the shoulder portion having an interior layer and an exterior layer, the interior layer having a plurality of foam supports secured thereto, the shoulder portion having an opening formed through the interior layer and the exterior layer adjacent to the foam supports whereby the plurality of foam supports surround the opening;

an elbow portion having securement straps securable around an arm of a patient, the elbow portion having an interior layer and an exterior layer, the interior layer having a plurality of foam supports secured thereto, the elbow portion having an opening formed through the interior layer and the exterior layer adjacent to the foam supports whereby the plurality of foam supports surround the opening;

an ankle portion having securement straps securable around a lower leg and foot of a patient, the ankle portion having an interior layer and an exterior layer, the interior layer having a plurality of foam supports secured thereto, the ankle portion having an opening formed through the interior layer and the exterior layer adjacent to the foam supports whereby the plurality of foam supports surround the opening;

a foot portion having a securement strap securable around a lower leg of a patient, the foot portion having an interior layer and an exterior layer, the interior layer having a plurality of foam supports secured thereto, the foot portion having an opening formed through the interior layer and the exterior layer adjacent to the foam supports whereby the plurality of foam supports surround the opening.

* * * * *